US006183621B1

(12) United States Patent
Görge et al.

(10) Patent No.: US 6,183,621 B1
(45) Date of Patent: *Feb. 6, 2001

(54) BASIC COBALTOUS CARBONATES, PROCESS FOR PREPARING THE SAME AND THEIR USE

(75) Inventors: Astrid Görge; Juliane Messe-Marktscheffel, both of Goslar (DE); Dirk Naumann, Ontario (CA); Armin Olbrich, Seesen (DE); Frank Schrumpf, Goslar (DE)

(73) Assignee: H. C. Stack GmbH & Co. KG, Goslar (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/981,079

(22) PCT Filed: May 14, 1996

(86) PCT No.: PCT/EP96/02051

§ 371 Date: Nov. 25, 1998

§ 102(e) Date: Nov. 25, 1998

(87) PCT Pub. No.: WO96/37437

PCT Pub. Date: Nov. 28, 1996

(30) Foreign Application Priority Data

May 26, 1995 (DE) .............................. 195 19 328

(51) Int. Cl.$^7$ .................... C25B 3/12; C25C 1/08; C01B 31/24
(52) U.S. Cl. .................. 205/480; 205/480; 205/509; 205/587; 423/419.1; 423/594; 252/182.1

(58) Field of Search ............... 252/182.1; 423/144, 423/149, 105.1, 140, 141, 419.1, 592, 594; 205/587, 588, 590, 509, 269, 480; 204/157.47, 157.5, 157.51, 158.2, 471, 489, 492, 493, 494, 498

(56) References Cited

U.S. PATENT DOCUMENTS 4,731,454 * 3/1988 Otake et al. ..................... 548/543

FOREIGN PATENT DOCUMENTS

| 0 353 837 A1 | 7/1990 | (EP) | ................. H01M/4/52 |
| 476232 | 3/1975 | (SU) . | |
| 684003 | 9/1979 | (SU) . | |

OTHER PUBLICATIONS

*Hawley's Condensed Chemical Dictionary*, 11th Ed., Van Nostrand Reinhold Company, N.Y. "Cobaltous Carbonate Basic" p. 293, 1987.*
Hawley's Condensed Chemical Dictionary, 11th Ed., Van Nostrand Reinhold Company, N.Y. "Cobaltic Oxide" p. 292, 1987.*
Hawley's Condensed Chemical Dictionary, 11th Ed., Van Nostrand Reinhold Company, N.Y. "Cobalt" p. 291, 1987.*
International Preliminary Examination Report Translation received in corresponding International Application PCT/EP96/02051 filed May 14, 1996.

(List continued on next page.)

*Primary Examiner*—Joseph D. Anthony
(74) *Attorney, Agent, or Firm*—Joseph C. Gil; Diderico van Eyl

(57) ABSTRACT

The present invention relates to processes for the production of cobalt(II) carbonates corresponding to the general formula $Co[(OH)_2]_a[CO_3]_{1-a}$, cobalt(II) carbonates and cobalt (II) oxalate carbonates obtainable by the process and the use thereof.

11 Claims, 1 Drawing Sheet

OTHER PUBLICATIONS

*Gmelins Handbuch der Anorganischen Chemie*, 8th edition, *Kobalt, Teil A*, 1932, Verlag Chemie, Berlin, pp. 237, 238, 347, 349.

PCT Search Report received in corresponding International Application PCT/EP 96/02049 filed May 14, 1996 and previously filed with the present application.

International Preliminary Examination Report Translation received in corresponding International Application PCT/EP96/02051 filed May 14, 1996.

*Gmelins Handuch der Anorganischen Chemie*, 8th edition, *Kobalt, Teil A*, 1932, Verlag Chemie, Berlin, pp. 437–440.

PCT Search Report received in corresponding International Application PCT/EP 96/02049 filed May 14, 1996 and previously filed with the present application.

*Gmelins Handbuch der Anorganischen Chemie*, 8th edition, *Kobalt, Teil A*, 1961, Verlag Chemie, Berlin, pp. 700–708.

*Gmelins Handbuch der Anorganischen Chemie*, 8th edition, *Kobalt, Teil A*, 1961, Verlag Chemie, Berlin, pp. 314–319.

* cited by examiner

BASIC COBALTOUS CARBONATES, PROCESS FOR PREPARING THE SAME AND THEIR USE

This is a 35 U.S.C. § 371 U.S. national phase entry of PCT/EP96/02051 filed internationally May 14, 1996.

The present invention relates to processes for the production of basic cobalt(II) carbonates corresponding to the general formula $Co[(OH)_2]_a[CO_3]_{1-a}$, cobalt(II) carbonates and cobalt(II) oxalate carbonates obtainable by the process and the use thereof.

Pure-phase cobalt(II) hydroxide is required for a number of industrial applications. For example, it can be used directly or after previous calcination to cobalt(II) oxide as a component in the positive electrode of modern heavy duty secondary batteries based on nickel/cadmium or nickel/metal hydride.

By means of cobaltates (II) which are formed as intermediaries and are soluble in the alkaline electrolytes of the battery (30% by weight of KOH), it is distributed uniformly in the electrode mass and deposited there by oxidation in the so-called forming cycles as electrically conductive CoO(OH) layer on the nickel hydroxide particles. Cobalt (III) contents present in the starting material do not form soluble cobaltates and are therefore unusable.

The use of cobalt compounds in alkaline secondary batteries based on nickel/cadmium or nickel/metal hydride is disclosed in EP-A 353837. Pure cobalt(II) oxides are also used as catalyst and in electronics.

Correspondingly pure basic cobalt(II) carbonates or hydroxides are used for the production of cobalt(II) salts of weak acids.

Cobalt(II) hydroxide can be produced by precipitation from aqueous cobalt(II) salt solutions with alkali liquors. The precipitates formed generally have a gel-like consistency and are difficult to filter and therefore difficult to wash free of neutral salts. Furthermore, they are very sensitive to oxidation in alkaline media, so filtration and washing processes have to be carried out while carefully excluding atmospheric oxygen.

Basic cobalt(II) carbonates are less sensitive to oxidation. They can be produced by precipitation from cobalt(II) salt solutions with alkali and/or ammonium carbonate solutions. Equimolar quantities of neutral salts are inevitably formed during precipitation. In order to wash the basic cobalt(II) carbonates obtained substantially free from neutral salts, it is necessary to use large quantities of washing water of up to 100 l per kg of cobalt.

Only impure cobalt raw materials of the type produced; for example, in the working up of cobalt-containing scrap are generally used for producing highly concentrated cobalt(II) salt solutions containing 100 to 200 g of Co/l, of the type used for the described precipitation processes. The comparatively low price of the cobalt in this scrap is in part lost again owing to the expensive cleaning processes.

High-purity cobalt raw materials of the type obtainable in an environmentally friendly and economical manner by electrolytic purification, for example in the form of cathodes, dissolve in highly concentrated hot mineral acids only with unsatisfactory space/time yields.

Anodic oxidation in an electrolysis process is possible for the production of cobalt hydroxides low in neutral salts. The discharge of these salts into the environment is minimized by circulation of the electrolyte solution containing the neutral salts.

Electrolysis processes of this type are described, for example, Gmelins Handbuch der Anorganischen Chemie, 8th edition (1961), Kobalt, Part A Supplement, pages 314–319. Cobalt(II) hydroxide produced in this way is very readily oxidized in the electrolytic cell to cobalt (III) hydroxide or cobalt (III) oxide hydroxide CoO(OH). Furthermore, these precipitates are difficult to filter and the neutral salt impurities in the product can be reduced only by the use of large amounts of washing water. However, the purities obtainable in this way generally remain unsatisfactory.

An object of the present invention was accordingly to provide a process for the production of basic cobalt(II) carbonates and cobalt(II) hydroxide which does not have the described disadvantages of the prior art, in particular from the ecological point of view.

It has now surprisingly been found that the oxidation of cobalt to cobalt (III) during electrolytic conversion is prevented if the pH of the electrolyte solution is stabilized in the weakly acidic to alkaline range by buffering with the $CO_3^{2-}/HCO_3^-/CO_2$ system. Owing to the supply of hydrogen carbonate and carbonate anions in addition to hydroxide anions in the electrolyte solution, the anodically oxidized cobalt which is more stable to oxidation than cobalt(II) hydroxide forms basic carbonates corresponding to the general formula $Co[(OH)_2]_a[CO_3]_{1-a}$.

This invention accordingly relates to a process for the production of basic cobalt(II) carbonates corresponding to the general formula $Co[(OH)_2]_a[CO_3]_{1-a}$, wherein metallic cobalt is anodically oxidized in aqueous $CO_2$-saturated electrolyte solutions and the basic cobalt(II) carbonate thus obtained is separated and washed.

By varying the composition of the electrolyte solution with respect to the supporting electrolytes, alkali metal chloride, alkali metal sulphate and alkali metal hydrogen carbonate or carbonate, it is possible substantially to optimize electrolysis with respect to electrolysis voltage and purity of the basic cobalt(II) carbonate produced. Anodic oxidation can be carried out under optimum conditions with current densities of up to 2000 $A·m^{-2}$. Space/time yields of up to 50 kg Co(II)/h·$m^3$ are therefore readily obtainable. Such space/time yields cannot be achieved by chemical dissolution, in particular of high-purity cobalt metal.

The electrolyte solutions preferably contains, as supporting electrolyte, alkali metal chlorides in a concentration range of 0.1 to 5 mol/l, preferably 0.2 to 2 mol/l and/or alkali sulphates in a concentration range of 0 to 0.1 mol/l and/or cobalt(II) chloride up to a maximum of 0.1 mol/l.

The process according to the invention is also particulary efficient if a content of alkali metal carbonates and/or hydrogen carbonates in a concentration range of 0.02 to 2 mol/l, preferably 0.1 to 1 mol/l is maintained in the electrolyte solutions. In the process according to the invention, the electrolyte solutions preferably have temperatures in the range of 5 to 80° C., preferably 10 to 30° C. End products with a smaller content of impurities are obtainable at lower temperatures. The pH of the electrolyte solutions should be kept in a range of 5 and 11, preferably 6 and 9.5.

The purity of the electrolytically obtained basic cobalt(II) carbonate according to the invention is also influenced by the residence time in the electrolysis process. The residence time of 1 h selected in examples 1 to 5 ensures that the sodium and chloride impurities can be washed out well.

When assessing the quantities of washing water to be used, it must be borne in mind that about 7 to 10 l of electrolyte solution per kg of Co are removed from the electrolysis process in the form of adherent moisture with the basic cobalt(II) carbonate. This quantity is displaced from the solid material again during the washing process, flows back into the electrolysis circuit and does not affect the waste water balance.

The hot mashing carried out in the subsequent working up of the filter cake causes a further reduction in the alkali and chloride values. Furthermore, $CO_2$ is liberated during heating of the basic cobalt(II) carbonates and can be recirculated directly into the electrolysis process for economic reasons. The separated basic cobalt(II) carbonate is therefore preferably mashed at temperatures between 50 and 100° C., filtered again and washed. Alkali liquors and/or ammonia can also advantageously be added during mashing. A further reduction in the chloride content can be achieved in this way. Substitution of the carbonate anion for hydroxide anions is also brought about in this way. Pure $Co(OH)_2$ can be obtained with an at least stoichiometric quantity of alkali liquors or ammonia.

Figure 1:
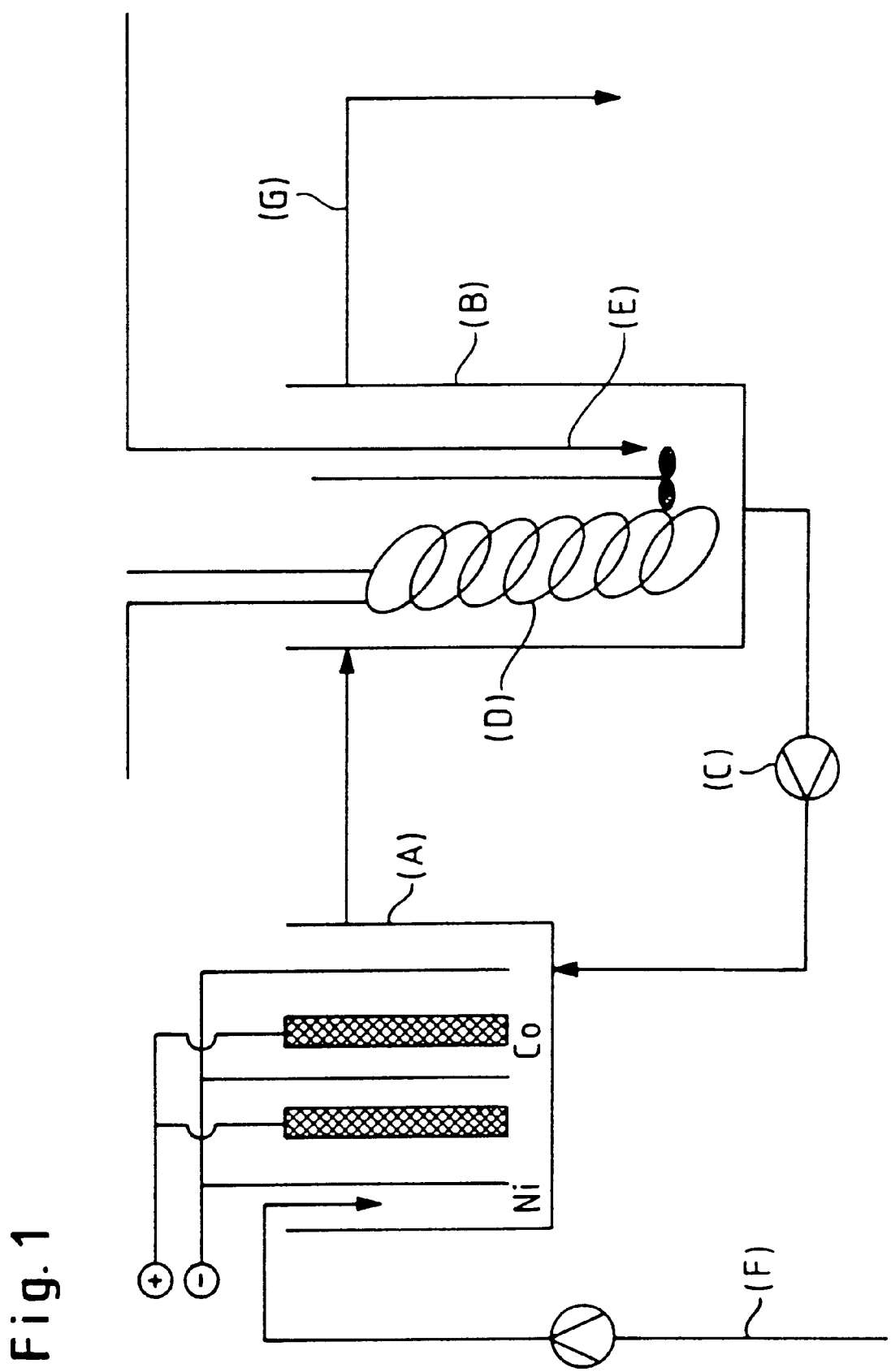
FIG. 1 is an elctrolysis apparatus of the type used to carry out the invention.

This invention accordingly relates to basic cobalt(II) carbonates corresponding to the general formula $Co[(OH)_2]_a[CO_3]_{1-a}$ which are obtainable by the process according to the invention. They preferably have a content of supporting electrolytes of <800 ppm, particularly preferably <200 ppm.

If electrolysis is carried out with addition of defined quantities of oxalic acid or oxalates, the corresponding oxalate-doped basic cobalt(II) carbonates corresponding to the general formula $Co[(OH)_2]_a[C_2O_4]_b[CO_3]_{1-a-b}$ can be obtained. No additional neutral salts are obtained when using oxalic acid.

This invention accordingly relates to basic cobalt(II) oxalate carbonates having the general composition $Co[(OH)_2]_a[C_2O_4]_b[CO_3]_{1-a-b}$, wherein $0 \leq a < 1$ and $0 < b \leq 1$.

This invention also relates to the use of the cobalt(II) carbonates according to the invention for the production of cobalt(II) oxides or partly reduced cobalt(II) oxides or cobalt metal powders by calcination and/or reduction.

This invention relates furthermore to the use of the basic cobalt oxalate carbonate for the production of cobalt metal-containing cobalt(II) oxides or cobalt metal powders by calcination and/or reduction. The cobalt metal-containing cobalt(II) oxides are suitable in particular for use in alkaline secondary batteries.

The invention is described hereinafter by way of non-limiting examples.

EXAMPLES 1–5

The tests were carried out in electrolysis apparatus of the type shown schematically in FIG. 1. This electrolysis apparatus consisted of the actual electrolytic cell (A) and a circulation container (B). The electrolyte/product suspension was pumped via the circulation container from below through the cell (A) by a centrifugal pump (C) in order to achieve thorough mixing.

A cooling coil (D) had been installed in the circulation container (B) in order to carry off resultant Joule heat. Carbon dioxide was also introduced into the electrolysis suspension through a frit (E). In order to guarantee the $CO_2$-saturation of the electrolysis solution before the beginning of electrolysis, $CO_2$ was introduced into the electrolysis solution for one hour before the electrolysis current was switched on. The cell (A) was supplied continuously with fresh electrolyte (F). The product suspension was continuously discharged via an overflow (G) on the circulation container (B).

The electrolysis cell (A) was charged with two anodes having an overall area of 1200 cm$^2$. Conventional commercial cobalt H electrodes were used. The cathodes of the electrolysis cell used consisted of 2 mm thick purest nickel or cobalt plates.

Samples were taken in each case after the solids concentration and temperature of the electrolysis suspension had reached a stationary state.

The mixture was worked up in that the product suspension continuously issuing from the circulation container (B) was filtered from the electrolyte over a nutsch filter and the filter cake washed in a first step with cold distilled water. In examples 1, 2 and 5 the filter cake thus obtained was subjected to further purification by mashing with hot distilled water or sodium hydroxide solution. The suspension was hot filtered, and the filter cake washed with water and dried at 80° C. in a drying cupboard to constancy of weight.

In examples 3 and 4 the filter cake thus obtained was subjected to further purification only by washing with 80° C. hot distilled water and was eventually dried at 80° C. in a drying cupboard to constancy of weight.

The electrolyte composition, the electrolysis conditions and the characteristic chemical analyses are compiled in the following Table 1.

The electrolysis processes described in Table 1 were carried out in an electrolytic cell having a gross volume of 5.0 l. 428.2 g of basic cobalt(II) carbonate per hour were formed with a current of 200 A (Example 2, Table 1). With a cobalt content of 51.1% by weight, this corresponds to 218.8 g of cobalt, corresponding to a current efficiency of 99.6%. Cathodic cobalt separation was not observed. Anodic chlorine evolution did not occur either. A space/time yield of 43.8 kg Co(II)/h·m$^3$ was obtained under these electrolysis conditions.

TABLE 1

| Example | Electrolyte | Electrolyte supply residence time | T [° C.] | pH | U [V] | I [A] j [A·m$^{-2}$] | Working up | Product |
|---|---|---|---|---|---|---|---|---|
| 1 | 100 g/l NaCl<br>10 g/l NaHCO$_3$ | 17 l/h.<br>1 h | 25 | 7.2–7.7 | 2.6 | 240,<br>2000 | -suction filtered<br>-cold washed with 25 l H$_2$O/kg Co<br>-mashed 10 min 80° C. 0.24 g/l NaOH<br>-suction filtered, washed with 10 l H$_2$O/kg Co | Co: 51.7% by weight<br>CO$_3^{2-}$: 21.9% by weight<br>Na: 40 ppm<br>Cl: 63 ppm |

TABLE 1-continued

| Example | Electrolyte | Electrolyte supply residence time | T [° C.] | pH | U [V] | I [A] j [A·m$^{-2}$] | Working up | Product |
|---|---|---|---|---|---|---|---|---|
| 2 | 50 g/l NaCl<br>25 g/l NaHCO$_3$<br>1.4 g/l Na$_2$SO$_4$ | 17 l/h<br>1 h | 15 | 7.8–9.3 | 4.3 | 200,<br>1670 | -suction filtered<br>-cold washed with 28 l H$_2$O/kg Co<br>-mashed 1 h 70° C., water<br>-suctioned filtered washed with 20 l H$_2$O/kg Co | Co: 51.1% by weight<br>CO$_3^{2-}$: 30.0% by weight<br>Na: 80 ppm<br>Cl: 20 ppm |
| 3 | 50 g/l Nacl<br>10 g/l NaHCO$_3$ | 17 l/h<br>1 h | 10 | 6.7–7.0 | 4.5 | 200,<br>1670 | -suction filtered<br>-cold washed with 30 l H$_2$O/kg Co<br>-mashed 15 l 80° C., water | Co: 53.4 Gew. %<br>CO$_3^{2-}$: 23.8 Gew %<br>Na: 5 ppm<br>Cl: 65 ppm |
| 4 | 50 g/l NaCl<br>15 g/l NaHCO$_3$ | 17 l/h<br>1 h | 10 | 6.9–7.3 | 4.4 | 200,<br>1670 | -suction filtered<br>-cold washed with 30 l H$_2$O/kg Co<br>-mashed 15 l 80° C., water | Co: 53.8 Gew %<br>CO$^{2-}$: 23.9 Gew %<br>Na: 7 ppm<br>Cl: 35 ppm |
| 5 | 100 g/l NaCl<br>10 g/l NaHCO$_3$<br>2.6 g/l H$_2$C$_2$O$_4$ | 17 l/h,<br>1 h | 10 | 7.3–7.8 | 2.9 | 140,<br>1170 | -suction filtered<br>-cold washed with 15 l H$_2$O/kg Co<br>-mashed 1 h 90° C., water<br>-suctioned filtered washed with 15 l H$_2$O/kg Co | Co: 46.3% by weight<br>CO$_3^{2-}$: 19.0% by weight<br>Na: 230 ppm<br>Cl: 70 ppm<br>Oxalate: 13.7% by weight |

EXAMPLE 6

Production of Cobalt(II) Hydroxide 500 g of the moist filter cake of the basic cobalt(II) carbonate from Example 1 with a Co content of 103 g were suspended in 700 ml of a 10% by weight sodium hydroxide solution and heated for 1 hour to 80° C. in an argon atmosphere. The suspension was hot-filtered, and the filter cake washed with 20 l of water per kg of cobalt. 170.8 g of pink-coloured powder were obtained after drying the filter cake at 80° C. in a vacuum drying cabinet. X-ray diffraction analysis showed a pure-phase Co(II) hydroxide. The Co content was found to be 60.3% by weight, the carbonate content was 0.27% by weight. The material had a chloride content of <20 ppm and a sodium content of 90 ppm.

EXAMPLE 7

Production of Cobalt Metal-containing Cobalt(II) Oxide 300 g of basic cobalt(II) carbonate from Example 5 were calcined at 620° C. for 2 hours in a quartz boat in an argon atmosphere. 171.4 g of light brown powder were obtained. In addition to cobalt(II) oxide, X-ray diffraction analysis revealed a small proportion of cubic and hexagonal cobalt metal. No Co(III) oxide could be detected. The cobalt content was found to be 82.0% by weight.

EXAMPLE 8

Production of Cobalt(II) Oxide 300 g of basic cobalt(II) carbonate from Example 2 were heated to 650° C. for 2 hours in a quartz boat in an argon atmosphere. 195.1 g of light brown powder were obtained. The cobalt content was 78.58% by weight. Only cobalt(II) oxide was detected in X-ray diffraction analysis.

EXAMPLE 9

Production of Cobalt Metal Powder 150 g of basic cobalt(II) carbonate from Example 2 were reduced for 3 hours at 650° C. in a quartz boat in a hydrogen atmosphere. On completion of reduction, the mixture was allowed to cool in an argon atmosphere. 77.0 g of dark grey powder were obtained. The cobalt content was found to be 99.6% by weight. The powder had an FSSS value of 2.8 μm.

What is claimed is:

1. A process for the production of basic cobalt (II) carbonate of the general formula Co[(OH)$_2$]$_a$[CO$_3$]$_{1-a}$ wherein $0.2 \leq a \leq 1$ by anodic oxidation of metallic cobalt in an aqueous CO$_2$ saturated electrolyte solution, and separating and washing the basic cobalt (II) carbonate product thus obtained, wherein the aqueous electrolyte solution further contains alkali carbonate and/or alkali hydrogen carbonate in a concentration range of 0.01 to 2 mol/l, and wherein the produced basic cobalt (II) carbonate has under 200 ppm electrolyte residue.

2. Process according to claim 1, characterized in that the electrolyte solutions contain, as supporting electrolyte, alkali metal chlorides in a concentration range of 0.1 to 5 mol/l.

3. Process according to claim 1, characterized in that the electrolyte solutions contain, as supporting electrolyte, alkali metal sulphates in a concentration range of 0 to 0.1 mol/l and/or cobalt(II) chloride up to a maximum of 0.1 mol/l.

4. Process according to claim 1, characterized in that the electrolyte solutions have temperatures in the range of 5 to 80° C.

5. Process according to claim 1, characterized in that a pH of between 5 and 11, is maintained in the electrolyte solutions.

6. Process according to claim 1, characterized in that the separated basic cobalt(II) carbonate is mashed at temperatures between 50 and 100° C., is filtered again and washed.

7. Process according to claim 1, characterized in that alkali liquors and/or ammonia are added during mashing.

8. The process of claim 1 with conditions thereof controlled to operate at about 1000–2000 A/m$^2$ current density and space-time yield of about 40–50 kg Co(II)/(h)(m$^3$) and to yield cobalt (II) carbonate products of substantial cobalt (II) form phase purity and under 200 ppm of electrolyte residue.

9. Process of producing cobalt (II) oxides or partially reduced cobalt (II) oxide or cobalt (II) powder by calcination of the carbonates of claim 1.

10. Process of producing cobalt (II) oxides or partially reduced cobalt (II) oxide or cobalt (II) powder by reduction of the carbonates of claim 1.

11. Process of producing cobalt (II) oxides or partially reduced cobalt (II) oxide or cobalt (II) powder by calcination and reduction of the carbonates of claim 1.

* * * * *